United States Patent
Fredebohm et al.

(10) Patent No.: US 9,845,507 B2
(45) Date of Patent: Dec. 19, 2017

(54) METHODS FOR DETECTING ONCOGENIC MUTATIONS

(71) Applicant: SYSMEX CORPORATION, Kobe-shi, Hyogo (JP)

(72) Inventors: Johannes Fredebohm, Hamburg (DE); Frank Diehl, Hamburg (DE); Frank Holtrup, Hamburg (DE); Daniel Mehnert, Hamburg (DE)

(73) Assignee: SYSMEX CORPORATION, Kobe-shi (JP)

( * ) Notice: Subject to any disclaimer, the term of this patent is extended or adjusted under 35 U.S.C. 154(b) by 410 days.

(21) Appl. No.: 14/501,159

(22) Filed: Sep. 30, 2014

(65) Prior Publication Data

US 2016/0090632 A1     Mar. 31, 2016

(51) Int. Cl.
*C12Q 1/68* (2006.01)

(52) U.S. Cl.
CPC ..... *C12Q 1/6886* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | | |
|---|---|---|---|---|
| 2003/0050470 A1* | 3/2003 | An | ........................ | C07H 21/00 536/24.3 |
| 2004/0023207 A1* | 2/2004 | Polansky | ............... | A61K 31/00 435/5 |
| 2012/0237485 A1 | 9/2012 | Du et al. | | |

FOREIGN PATENT DOCUMENTS

| WO | WO 2012/142213 | 10/2012 |
|---|---|---|
| WO | WO 2013/081864 | 6/2013 |

OTHER PUBLICATIONS

Debiec-Rychter et al. KIT mutations and dose selection for imatinib in patients with advanced gastrointestinal stromal tumours. European Journal of Cancer 42:1093-1103 (2006).*
GenBank accession No. NG_007456 [online] Sep. 3, 2013 [retrieved on Nov. 4, 2016] retrieved from: https://www.ncbi.nlm.nih.gov/nuccore/170014706?sat=17&satkey=26024803.*
Heinrich et al. Kinase mutations and imatinib response in patients with metastatic gastrointestinal stromal tumor. Journal of Clinical Oncology 21(23):4342-4349 (2003).*
Santa Lucia, J. PCR Primer Design. Methods in Molecular Biology 402. Edited by Anton Yuryev, Humana Press (2007); front matter and pp. 3-33 (40 total pages).*
Kinde et al. Detection and quantification of rare mutations with massively parallel sequencing. PNAS 108(23):9530-9535 (2011).*
Thomas et al.High-throughput oncogene mutation profiling in human cancer. Nature Genetics 39:347-351 (2007).*
Thomas et al Supplementary Table 1 [online] 2007 [retrieved on Nov. 7, 2016] retrieved from http://www.nature.com/ng/journal/v39/n3/suppinfo/ng1975_S1.html.*
Matthews & Gerritsen (2010) Appendix IX: Tumor Associated Mutations in Kit, in Targeting Protein Kinases for Cancer Therapy, John Wiley & Sons, Inc. Hoboken, NJ, USA (14 pages).*
Hersmus et al., "Prevalence of c-KIT mutations in gonadoblastoma and dysgerminomas of patients with disorders of sex development (DSD) and ovarian dysgerminomas," *PLoS One*, 7(8):e43952, 2012.
Lovly et al., "Routine multiplex mutational profiling of melanomas enables enrollment in genotype-driven therapeutic trials," *PLoS One*, 7(4):e35309, 2012.

* cited by examiner

*Primary Examiner* — Samuel Woolwine
(74) *Attorney, Agent, or Firm* — Parker Highlander PLLC

(57) ABSTRACT

Provided herein are methods for the detection of genetic mutations associated with cancer, particularly in the KIT gene.

10 Claims, 6 Drawing Sheets

METHODS FOR DETECTING ONCOGENIC MUTATIONS

INCORPORATION OF SEQUENCE LISTING

The sequence listing that is contained in the file named "ISTCP0005US_ST25.txt", which is 15 KB (as measured in Microsoft Windows®) and was created on Sep. 23, 2014, is filed herewith by electronic submission and is incorporated by reference herein.

BACKGROUND OF THE INVENTION

1. Field of the Invention

The present invention relates to a reagent kit and a method for detecting a mutation of a KIT gene.

2. Description of Related Art

It is known that mutations of KIT gene can be a marker of specific disease such as a cancer. It has been detected by various conventional methods. For instance, next generation sequencing (NGS) has been used for it. In conventional NGS, the errors introduced by polymerases cannot be distinguished from sequence alterations of the original template molecules.

SUMMARY OF THE INVENTION

Herein, a highly sensitive and reliable method of detecting DNA sequence aberrations in the KIT gene is provided.

The primers used for UID-PCR are, in some aspects, used in multiplex for the production of template for a Well-Barcode-PCR (WBC-PCR). These primers comprise, or consist of, a universal sequence (e.g., a WBC-PCR primer binding site), the digital unique identifier (UID), and a gene-specific binding site (which is hereinafter also called "complementary sequence portion").

In one embodiment, a method is provided to analyze a biological sample from an organism for genetic mutations associated with cancer, the method comprising performing multiplex sequencing of DNA amplified with at least two panels of primers, wherein the at least two panels of primers comprise primers that amplify at least two amplicons of a gene with genetic mutations. In certain aspects, a method of the embodiments is defined as an in vitro method.

In some aspects, the gene may be KIT (see e.g., SEQ ID NO: 49). In this aspect, the at least two amplicons of KIT may be comprised in exons 8-11, 13, 14, 17, and/or 18. In some aspects, a first panel of primers may amplify at least two amplicons selected from the group consisting of amplicons generated by amplification reactions performed with primer pair IDs 24, 36, 39, 52, 55, and 56 of Table 1 and a second panel of primers may amplify at least two amplicons selected from the group consisting of amplicons generated by amplification reactions performed with primer pair IDs 12, 47, 54, 61, and 62 of Table 1. In some aspects, an amplicon may be shifted 1, 2, 3, 4, 5, 6, 7, 8, 9, 10, 11, 12, 13, 14, 15, 16, 17 18, 19 or 20 base pairs upstream or downstream of the amplicon as defined by the primers shown in Table 1. In certain aspects, the amplification of the amplicons is carried out using primer pairs at least 85% identical to those listed in Table 1. In some aspects, 1, 2, 3, 4 or 5 base pairs may be different than the base pairs listed in Table 1 for a given primer. In other aspects, a primer may comprise or consist of the sequences as listed in Table 1.

In a further embodiment, a kit is provided comprising primer pairs for amplification of amplicons generated by amplification reactions performed with primer pair IDs 24, 36, 39, 52, 55, and 56 or amplicons generated by amplification reactions performed with primer pair IDs 12, 47, 54, 61, and 62 of the KIT gene as listed in Table 1. In certain aspects, the kit may comprise primer pairs for amplification of amplicons generated by amplification reactions performed with primer pair IDs 24, 36, 39, 52, 55, and 56 and amplicons generated by amplification reactions performed with primer pair IDs 12, 47, 54, 61, and 62 of the KIT gene as listed in Table 1. In some aspects, an amplicon may be shifted 1, 2, 3, 4, 5, 6, 7, 8, 9, 10, 11, 12, 13, 14, 15, 16, 17 18, 19 or 20 base pairs upstream or downstream of the amplicon as defined by the primers shown in Table 1. In certain aspects, the primer pairs may be at least 85% identical to those listed in Table 1. In some aspects, 1, 2, 3, 4 or 5 base pairs may be different than the base pairs listed in Table 1 for a given primer. In other aspects, a primer may comprise or consist of the sequences as listed in Table 1.

In still a further embodiment, a reagent kit is provided for detecting a mutation of a KIT gene in a specimen comprising DNA, the kit comprising at least one primer set selected from the group consisting of: a) a forward primer comprising a sequence of SEQ ID NO: 1 and a reverse primer comprising a sequence of SEQ ID NO: 2; b) a forward primer comprising a sequence of SEQ ID NO: 3 and a reverse primer comprising a sequence of SEQ ID NO: 4; c) a forward primer comprising a sequence of SEQ ID NO: 5 and a reverse primer comprising a sequence of SEQ ID NO: 6; d) a forward primer comprising a sequence of SEQ ID NO: 7 and a reverse primer comprising a sequence of SEQ ID NO: 8; e) a forward primer comprising a sequence of SEQ ID NO: 9 and a reverse primer comprising a sequence of SEQ ID NO: 10; f) a forward primer comprising a sequence of SEQ ID NO: 11 and a reverse primer comprising a sequence of SEQ ID NO: 12; g) a forward primer comprising a sequence of SEQ ID NO: 13 and a reverse primer comprising a sequence of SEQ ID NO: 14; h) a forward primer comprising a sequence of SEQ ID NO: 15 and a reverse primer comprising a sequence of SEQ ID NO: 16; i) a forward primer comprising a sequence of SEQ ID NO: 17 and a reverse primer comprising a sequence of SEQ ID NO: 18; j) a forward primer comprising a sequence of SEQ ID NO: 19 and a reverse primer comprising a sequence of SEQ ID NO: 20; or k) a forward primer comprising a sequence of SEQ ID NO: 21 and a reverse primer comprising a sequence of SEQ ID NO: 22.

In some aspects, the kit may comprise at least two, three, four, or five primer sets selected from the group consisting of primer sets b), c), d), f), h), and i). In certain aspects, the kit may comprise primer sets b), c), d), f), h), and i). In some aspects, the kit may comprise at least two, three, or four primer sets selected from the group consisting of primer sets a), e), g), j), or k). In a further aspect, the kit may comprise primer sets a), e), g), j), and k). In some aspects, the kit may comprise at least two, three, four, five, six, seven, eight, nine, or ten of primer sets selected from the group consisting of primer sets a)-k). In yet a further aspect, the kit may comprise primer sets a)-k). In various aspects, at least one primer in the primer set may comprise a heterologous nucleotide sequence. In certain aspects, the heterologous nucleotide sequence may be a M13 Forward or M13 Reverse sequence. In some aspects, at least one primer in the primer set may comprise a sequence of SEQ ID NO: 45 or a sequence of SEQ ID NO: 46.

In various aspects, one primer in the primer set may comprise a random sequence. In some aspects, the random sequence may comprise 10-18 random nucleotides (e.g., 10, 11, 12, 13, 14, 15, 16, 17 or 18). In some aspects, the random sequence is a known sequence. In certain aspects, the primer in the primer set that comprises a random sequence may further comprise a sequence of SEQ ID NO: 45. In certain aspects, the primer in the primer set that does not comprise a random sequence may further comprise a sequence of SEQ ID NO: 46. In certain aspects, one primer in the primer set may comprise a random sequence and a sequence of SEQ ID NO: 45. In certain aspects, one primer in the primer set may comprise a sequence of SEQ ID NO: 45 and the other primer in the primer set may comprise a sequence of SEQ ID NO: 46.

In a further aspect, a primer set a) may be further defined as a forward primer comprising a sequence of SEQ ID NO: 41 and a reverse primer comprising a sequence of SEQ ID NO: 42. In one aspect, primer set b) may be further defined as a forward primer comprising a sequence of SEQ ID NO: 27 and a reverse primer comprising a sequence of SEQ ID NO: 28. In one aspect, primer set c) may be further defined as a forward primer comprising a sequence of SEQ ID NO: 25 and a reverse primer comprising a sequence of SEQ ID NO: 26. In one aspect, primer set d) may be further defined as a forward primer comprising a sequence of SEQ ID NO: 33 and a reverse primer comprising a sequence of SEQ ID NO: 34. In one aspect, primer set e) may be further defined as a forward primer comprising a sequence of SEQ ID NO: 37 and a reverse primer comprising a sequence of SEQ ID NO: 38. In one aspect, primer set f) may be further defined as a forward primer comprising a sequence of SEQ ID NO: 23 and a reverse primer comprising a sequence of SEQ ID NO: 24. In one aspect, primer set g) may be further defined as a forward primer comprising a sequence of SEQ ID NO: 39 and a reverse primer comprising a sequence of SEQ ID NO: 40. In one aspect, primer set h) may be further defined as a forward primer comprising a sequence of SEQ ID NO: 31 and a reverse primer comprising a sequence of SEQ ID NO: 32. In one aspect, primer set i) may be further defined as a forward primer comprising a sequence of SEQ ID NO: 29 and a reverse primer comprising a sequence of SEQ ID NO: 30. In one aspect, primer set j) may be further defined as a forward primer comprising a sequence of SEQ ID NO: 35 and a reverse primer comprising a sequence of SEQ ID NO: 36. In one aspect, primer set k) may be further defined as a forward primer comprising a sequence of SEQ ID NO: 43 and a reverse primer comprising a sequence of SEQ ID NO: 44.

In some aspects, the specimen may be selected from the group consisting of a tissue biopsy, resected tumor and a bodily fluid, such as, for example, a lymph, saliva, blood (e.g., serum or plasma) or urine sample. In some aspects, a sample may be fractionated to purify DNA from other components. In certain aspects, the specimen may be a human specimen. In one aspect, the KIT gene may comprise a sequence of SEQ ID NO: 49.

In still a further embodiment, a method is provided for detecting (or selectively detecting) a mutation of a KIT gene comprising amplifying KIT gene DNA using the reagent kit according to the present embodiment, thereby detecting the mutation of the KIT gene. In some aspects, the mutation may be a point mutation, insertion, or deletion.

In a further aspect, a method of detecting (or selectively detecting) a mutation of the KIT gene comprises identifying a mutation that is present in a threshold portion of amplicons (within one UID-family). Such a method can, for example, allow for mutations present in the nucleic acids of the sample to be distinguished from mutations that can arise from errors introduced by the polymerase during amplification. For example, in some aspects, detecting a mutation comprises identifying mutation s present in at least about 10%, 20%, 30%, 40%, 50%, 60%, 70%, 80%, or 90% (e.g., between about 50% and about 90%) of the amplicons (in a given UID family). In certain aspects, the mutation is present in at least 70%, 75%, 80%, 85%, or 90% of these amplicons.

In certain aspects, the mutations may be associated with cancer and the method may be further defined as a method of detecting and/or monitoring cancer. Types of tumors that can be detected and/or monitored in this fashion are virtually unlimited. Any tumor that sheds cells and/or DNA into the blood or stool or other bodily fluid can be used. Such tumors include, in addition to colorectal tumors, tumors of the breast, lung, kidney, liver, pancreas, stomach, brain, head and neck, lymphatics, ovaries, uterus, bone, blood, etc.

In certain aspects, the method may be further defined as a method of detecting susceptibility or resistance to therapies that target kit. For example, in some aspects, a method of the embodiments is defined as a method of detecting resistance to drugs targeting KIT. Kit targeting drugs include, without limitation 2-phenylpyrimidine tyrosine kinase inhibitors, such as imatinib (STI-571) and (2-carboxyamido)(3-amino)thiophene compounds (see, e.g., U.S. Pat. No. 6,949,563 and U.S. Pat. Publication No. 2005/0154014, each incorporated herein by reference). For example, in some specific aspects the Kit targeting drug is imatinib, OSI-930, OSI-817, AMG 706, AMN 107 (nilotinib), sunitinib, sorafenib, dasatinib, pazopanib, ponatinib, regorafenib or masitinib (AB 1010).

In still further aspects, a method further comprises reporting mutations of a KIT gene detected in a sample or reporting whether a subject is susceptible or resistant to a therapy that targets KIT. Reporting may comprise preparing an oral, written or electronic report. In some aspects, such a report is provided to the patient, a doctor, a hospital, or an insurance company.

As used herein the phrase "selectively determining" refers to methods wherein only a finite number of genes are assessed for mutations (e.g., rather than assaying essentially all genes in a sample). For example, in some aspects "selectively determining" a gene mutation can refer to assessing mutations in no more than 10, 8, 7, 6, 5, 4, 3, 2 or 1 different genes in a sample. In some aspects a method of the embodiments comprises detecting mutations in a gene, the gene consisting of the KIT gene.

In a still a further embodiment there is provided an isolated nucleic acid molecule comprising, or consisting of, the sequence of any one of SEQ ID NOs: 107-132. In further aspects, the isolated nucleotide molecule is no more than 200, 150, 100 or 75 nucleotides in length. In certain aspects, the nucleic acid molecule comprises a heterologous (e.g., non-human) sequence. For example, the heterologous sequence may comprise a random nucleotide sequence such as a random sequence of 10-18 nucleotides. In some aspects, the heterologous sequence comprises the sequence of SEQ ID NO: 45 or 46. In a yet a further aspect, an isolated nucleotide molecule of the embodiments comprises, or consists of, the sequence of any one of SEQ ID NOs: 23-44.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present embodiments will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. Embodiments of the invention may be better understood by reference to one or more of these drawings in combination with the detailed description of specific embodiments presented herein.

DESCRIPTION OF ILLUSTRATIVE EMBODIMENTS

Embodiments of the present invention use a digital unique identifier (UID)-PCR to label each and every amplicon of interest with a unique barcode sequence while it is being produced. These barcoded amplicons are again amplified to generate UID families. By means of NGS and subsequent data analysis, mutation detection takes place within each UID family. A sequence alteration is reported only if it is carried in more than a set threshold of all UID family members, thus minimizing false positive results. Polymerase errors occurring during UID-PCR are further reduced by setting individual background-thresholds for every nucleotide position. These are determined by using the same approach on wild-type DNA from healthy individuals.

In various aspects, the UID-primers may amplify mutation hotspots in KIT. Due to the multiplexing of large stretches of KIT DNA, several mutations in KIT can be detected from a single plasma sample.

I. KIT GENE

The KIT gene, the complete open reading frame of which is provided in SEQ ID NO: 49, has the official gene name: v-kit Hardy-Zuckerman 4 feline sarcoma viral oncogene homolog. KIT is also known as proto-oncogene c-Kit, tyrosine-protein kinase Kit, or CD117. In this specification, this gene is called either "KIT" or "KIT gene."

II. AMPLICONS AND PRIMERS

The reagent kit according to the present embodiments comprises a plurality of primer sets. Each primer set comprises forward and reverse primers. The forward primer comprises a complementary sequence portion that is substantially complementary to an antisense strand of KIT from which nucleic acid amplification starts. The reverse primer comprises a complementary sequence portion that is substantially complementary to a sense strand of KIT from which nucleic acid amplification starts.

For Safe-Sequencing, the forward primer preferably comprises a UID sequence. The UID can be a random sequence. The UID sequence is preferably located 5' of the complementary sequence portion of the forward primer. More preferably, the forward primer comprises a universal sequence. One example of a universal sequence is the first M13 sequence. The first M13 sequence is preferably located 5' of the UID sequence.

The reverse primer preferably comprises a universal sequence. One example of a universal sequence is the second M13 sequence. The second M13 sequence is preferably located 5' of the complementary sequence portion of the reverse primer. The reverse primer can also comprise a UID sequence. The UID sequence can be located between the second M13 sequence and the complementary sequence portion in the reverse primer.

Figure 2:
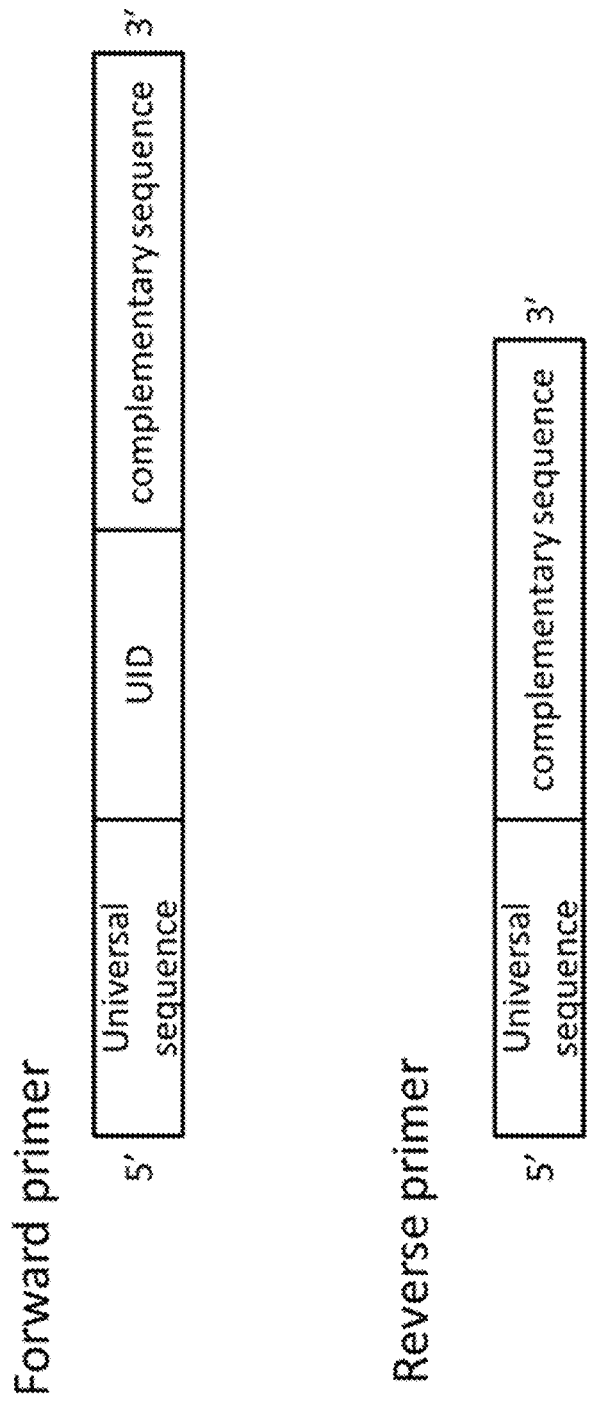
FIG. 2. Schematic illustration of the forward primer, which comprises the universal sequence, UID, and complementary sequence portion, and the reverse primer, which comprises the universal sequence.

FIG. 2 is a schematic illustration of a forward primer, which comprises the universal sequence, UID, and complementary sequence portion, and a reverse primer, which comprises the universal sequence. Table 3, below shows the exon structure (i.e., the beginning and ending position of each exon) of the KIT gene for analysis by the methods of the embodiments.

TABLE 1

KIT Primers

| Primer pair ID | Complementary sequence portion of Forward Primer | SEQ ID NO: | Complementary sequence portion of Reverse Primer | SEQ ID NO: | UID Location* |
|---|---|---|---|---|---|
| 12 | ATTATTGACTCTGT TGTGCTTCTATTAC AG | 1 | ACGTCACTTTCAA ACGTGTATACAC | 2 | reverse |
| 24 | TACAACGATGTGGG CAAGAC | 3 | GACAGAGCCTAAA CATCCCC | 4 | forward |
| 36 | CCATTTGACAGAAC GGGAAG | 5 | ACACGGCTTTACC TCCAATG | 6 | forward |

TABLE 1 -continued

KIT Primers

| Primer pair ID | Complementary sequence portion of Forward Primer | SEQ ID NO: | Complementary sequence portion of Reverse Primer | SEQ ID NO: | UID Location* |
|---|---|---|---|---|---|
| 39 | CCTTTTCTTATGTG CTTTTAGGG | 7 | AAATAAATGAATC ACGTTTTCTTCTC | 8 | forward |
| 47 | TGGCCATTTCTGTT TTCCTG | 9 | TGCTGCCACACAT TGGAG | 10 | reverse |
| 52 | TCTATTTTTCCCTT TCTCCCC | 11 | GGGTCTATGTAAA CATAATTGTTTCC | 12 | forward |
| 54 | GCTGATTGGTTTCG TAATCGT | 13 | TCTGGAGAGAGAA CAAATAAATGG | 14 | forward |
| 55 | ACTCATGGTCGGAT CACAAA | 15 | GCAGGACTGTCAA GCAGAGA | 16 | forward |
| 56 | CTTCCTTATGATCA CAAATGGGAG | 17 | GGTGACATGGAAA GCCCC | 18 | reverse |
| 61 | AAGTACAGTGGAAG GTTGTTGAGG | 19 | AAACTCAGCCTGT TTCTGGG | 20 | forward |
| 62 | CTAATAGTGTATTC ACAGAGACTTGGC | 21 | TGGCTAGACCAAA ATCACAAATC | 22 | forward |

*Orientation refers to the location of the randomized 14-base UID sequence, whether it is connected to the forward or the reverse primer.

Primers for use with the embodiments may be fused to the M13 sequence at their 5' end as follows:

M13 forward:
(SEQ ID NO: 45)
5'-CGACGTAAAACGACGGCCAGT-3';

M13 reverse:
(SEQ ID NO: 46)
5'-CACACAGGAAACAGCTATGACCATG-3'.

The forward or the reverse primer may be fused with either one of these sequences.

Primer sequences used to amplify the UID assigned products may be as follows (* stands for a phosphodiester bond; "N" stands for any of A, T, G and C):

Forward:
(SEQ ID NO: 47)
5'-AATGATACGGCGACCACCGAGATCTACACCGACGTAAAACGACGGCC

A*G*T-3';

Reverse:
(SEQ ID NO: 48)
5'-CAAGCAGAAGACGGCATACGAGATNNNNNNNCACACAGGAAACAGCTA

TGACCA*T*G-3'.

III. METHODS OF MULTIPLEX SEQUENCING—SAFE-SEQUENCING

Primers of the present embodiment can be used for Safe-Sequencing, which involves two steps: (1) library preparation is performed by using uniquely-tagged primers (UID-Primers), labeling each nascent molecule in a first PCR (UID-PCR); and (2) amplification of each uniquely tagged template so that many daughter molecules with the identical sequence are generated (defined as a UID-family) (see WO 2012/142213, which is incorporated herein by reference in its entirety). If a mutation pre-existed in the template molecule used for amplification, that mutation should be present in a certain proportion, or even all, of daughter molecules containing that UID (barring any subsequent replication or sequencing errors). A UID-family in which every family member (or a certain predetermined proportion) has an identical mutation is called a "super-mutant." Mutations not occurring in the original templates, such as those occurring during amplification steps after UID-PCR or through errors in base-calling, should not give rise to super-mutants, i.e., will not be present at the predetermined frequency in a UID-family.

In some cases, by iteratively applying Safe-Sequencing to wild-type DNA samples, the background polymerase error rate can be determined. Under the premise that the template molecules contain no sequence aberrations (i.e., are wild-type), the super-mutants detected with known wild-type DNA can only originate from polymerase errors occurring during the UID-PCR.

By applying these approaches Safe-Sequencing data is more reliable than data from conventional NGS, and fewer false positive mutations are reported. In addition, Safe-Sequencing provides for detection of previously unknown mutations. The approach can be employed for any purpose where a very high level of accuracy and sensitivity is required from sequence data. As shown below, the approach can be used to assess the fidelity of a polymerase, the accuracy of in vitro synthesized nucleic acid synthesis, and the prevalence of mutations in nuclear or mitochondrial nucleic acids of normal cells. The approach may be used to detect and/or quantify mosaicism, germline and somatic mutations.

Fragments of nucleic acids may be obtained using a random fragment forming technique such as mechanical shearing, sonicating, or subjecting nucleic acids to other physical or chemical stresses. Fragments may not be strictly random, as some sites may be more susceptible to stresses than others. Endonucleases that randomly or specifically fragment may also be used to generate fragments. Size of fragments may vary, but desirably will be in ranges between 30 and 5,000 basepairs, between 100 and 2,000, between 150 and 1,000, or within ranges with different combinations of these endpoints. Nucleic acids may be, for example, RNA or DNA. Modified forms of RNA or DNA may also be used.

Attachment of an exogenous UID to an analyte nucleic acid fragment may be performed by any means known in the art, including enzymatic, chemical, or biologic. One means employs a polymerase chain reaction. Another means employs a ligase enzyme. The enzyme may be mammalian or bacterial, for example. Ends of fragments may be repaired prior to joining using other enzymes such as Klenow Fragment of T4 DNA Polymerase. Other enzymes which may be used for attaching are other polymerase enzymes. A UID may be added to one or both ends of the fragments. A UID may be contained within a nucleic acid molecule that contains other regions for other intended functionality. For example, a universal priming site may be added to permit later amplification. Another additional site may be a region of complementarity to a particular region or gene in the analyte nucleic acids. A UID may be from 2 to 4,000, from 100 to 1000, from 4 to 400, bases in length, for example.

UIDs may be made using random addition of nucleotides to form a short sequence to be used as an identifier. At each position of addition, a selection from one of four deoxyribonucleotides may be used. Alternatively a selection from one of three, two, or one deoxyribonucleotides may be used. Thus the UID may be fully random, somewhat random, or non-random in certain positions. Another manner of making UIDs utilizes pre-determined nucleotides assembled on a chip. In this manner of making, complexity is attained in a planned manner. It may be advantageous to attach a UID to each end of a fragment, increasing the complexity of the UID population on fragments.

A cycle of polymerase chain reaction for adding exogenous UID refers to the thermal denaturation of a double stranded molecule, the hybridization of a first primer to a resulting single strand, the extension of the primer to form a new second strand hybridized to the original single strand. A second cycle refers to the denaturation of the new second strand from the original single strand, the hybridization of a second primer to the new second strand, and the extension of the second primer to form a new third strand, hybridized to the new second strand. Multiple cycles may be required to increase efficiency, for example, when analyte is dilute or inhibitors are present.

In the case of endogenous UIDs, adapters can be added to the ends of fragments by ligation. Complexity of the analyte fragments can be decreased by a capture step, either on a solid phase or in liquid step. Typically the capture step will employ hybridization to probes representing a gene or set of genes of interest. If on a solid phase, non-binding fragments are separated from binding fragments. Suitable solid phases known in the art include filters, membranes, beads, columns, etc. If in a liquid phase, a capture reagent can be added which binds to the probes, for example through a biotin-avidin type interaction. After capture, desired fragments can be eluted for further processing. The order of adding adapters and capturing is not critical. Another means of reducing the complexity of the analyte fragments involves amplification of one or more specific genes or regions. One way to accomplish this is to use inverse PCR. Primers can be used which are gene-specific, thus enriching while forming libraries. Optionally, the gene-specific primers can contain grafting sequences for subsequent attachment to a massively parallel sequencing platform.

Because endogenous UIDs provide a limited number of unique possibilities, depending on the fragment size and sequencing read length, combinations of both endogenous and exogenous UIDs can be used, introducing additional sequences when amplifying would increase the available UIDs and thereby increase sensitivity. For example, before amplification, the template can be split into 96 wells, and 96 different primers could be used during the amplification. This would effectively increase the available UIDs 96-fold, because up to 96 templates with the same endogenous UID could be distinguished. This technique can also be used with exogenous UIDs, so that each well's primers add a unique, well-specific sequence to the amplification products. This can improve the specificity of detection of rare templates.

Amplification of fragments containing a UID can be performed according to known techniques to generate families of fragments. Polymerase chain reaction can be used. Other amplification methods can also be used, as is convenient. Inverse PCR may be used, as can rolling circle amplification. Amplification of fragments typically is done using primers that are complementary to priming sites that are attached to the fragments at the same time as the UIDs. The priming sites are distal to the UIDs, so that amplification includes the UIDs. Amplification forms a family of fragments, each member of the family sharing the same UID. Because the diversity of UIDs is greatly in excess of the diversity of the fragments, each family should derive from a single fragment molecule in the analyte. Primers used for the amplification may be chemically modified to render them more resistant to exonucleases. One such modification is the use of phosphorothioate linkages between one or more 3' nucleotides.

Family members are sequenced and compared to identify any divergencies within a family. Sequencing is preferably performed on a massively parallel sequencing platform, many of which are commercially available. If the sequencing platform requires a sequence for "grafting," i.e., attachment to the sequencing device, such a sequence can be added during addition of UIDs or adapters or separately. A grafting sequence may be part of a UID primer, a universal primer, a gene target-specific primer, the amplification primers used for making a family, or separate. Redundant sequencing refers to the sequencing of a plurality of members of a single family.

A threshold can be set for identifying a mutation in an analyte. If the "mutation" appears in all members of a UID-family, then it derives from the analyte. If it appears in less than all members, then it may have been introduced during the analysis. Thresholds for calling a mutation may be set, for example, at 1%, 5%, 10%, 20%, 30%, 40%, 50%, 60%, 70%, 80%, 90%, 95%, 97%, 98%, or 100%. Thresholds will be set based on the number of members of a UID-family that are sequenced and the particular purpose and situation.

Populations of primer pairs are used to attach exogenous UIDs. The first primer comprises a first portion of 10-100 nucleotides complementary to the gene or gene portion and a second portion of 10 to 100 nucleotides comprising a site for hybridization to a third primer. The second primer comprises a first portion of 10-100 nucleotides complementary to the gene or gene portion and a second portion of 10 to 100 nucleotides comprising a site for hybridization to a fourth primer. Interposed between the first portion and the second portion of the second primer is a third portion consisting of 2 to 4,000 nucleotides forming a unique identifier (UID). The unique identifiers in the population have at least 4, at least 16, at least 64, at least 256, at least 1,024, at least 4,096, at least 16,384, at least 65,536, at least 262,144, at least 1,048,576, at least 4,194,304, at least 16,777,216, or at least 67,108,864 different sequences. The first and second primers are complementary to opposite strands of the gene or gene portion. A kit can be made containing both the primers for attaching exogenous UIDs as well as amplification primers, i.e., the third and fourth primers complementary to the second portions of each of the first and second primers. The third and fourth primers can optionally contain additional grafting or indexing sequences. The UID may comprise randomly selected sequences, pre-defined nucleotide sequences, or both randomly selected sequences and pre-defined nucleotides. If both, these can be joined together in blocks or interspersed.

IV. EXAMPLES

The following examples are included to demonstrate preferred embodiments of the invention. It should be appreciated by those of skill in the art that the techniques disclosed in the examples which follow represent techniques discovered by the inventor to function well in the practice of embodiments of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—KIT Panel Assembly

Figure 1:
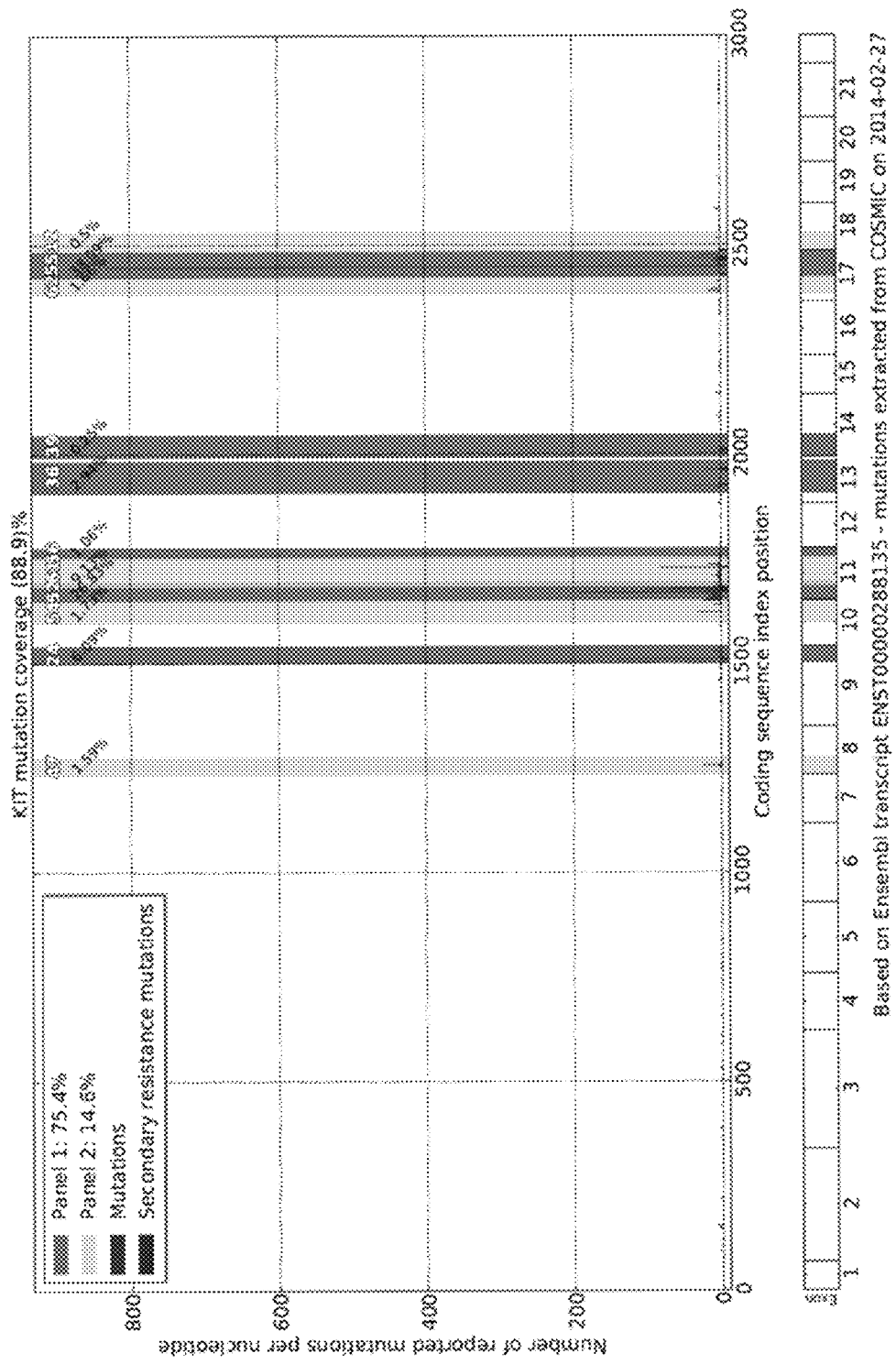
FIG. 1. KIT composite mutation coverage (88.9%). Based on Ensembl transcript ENST00000288135. X-axis represents the nucleotide sequence of the transcript relative to the start codon. Y-axis represents the mutation count. Dark gray bands are Panel 1; light gray bands are Panel 2. Histogram spikes represent mutations. Vertical black bars above X-axis represent possible secondary resistance mutations to imatinib. White numbers at the top of each band (from the left, 47, 24, 54, 52, 61, 56, 36, 39, 62, 55, and 12) correspond to the Primer pair ID number in Tables 1 and 2. Bar across bottom represents the exon structure of the transcript and correspond to the nucleotide positions provided in Table 3.

Two panels of KIT amplicons defined by the primers of Table 1 were generated and found to provide 88.9% mutation coverage of the KIT gene (as illustrated in FIG. 1). Primer pair ID 47 covers 1.59% of mutations; primer pair ID 24 covers 5.09% of mutations; primer pair ID 54 covers 1.73% of mutations; primer pair ID 52 covers 26.83% of mutations; primer pair ID 61 covers 9.13% of mutations; primer pair ID 56 covers 1.06% of mutations; primer pair ID 36 covers 2.94% of mutations; primer pair ID 39 covers 0.25% of mutations; primer pair ID 62 covers 1.66% of mutations; primer pair ID 55 covers 38.09% of mutations; primer pair ID 12 covers 0.5% of mutations) The primer sequences for these panels are listed in Table 2, below ("N" in Sequence is any of A, T, G and C; a sequence portion consisting of plural "N"s in each primer sequence is a random sequence). The combined use of the two panels provided coverage of mutations in exons 8-11, 13, 14, 17, and 18 of the KIT gene. The KIT transcript (corresponding to open reading frame of ENST00000288135; SEQ ID NO: 49) is composed of the exon domains of the gene sequence as shown in Table 3.

TABLE 2

KIT Primer Panel Sequences

| Panel | Primer pair ID | Primer ID | Sequence | UID primer position | SEQ ID NO: |
|---|---|---|---|---|---|
| KIT_1 | KIT52 | IN2833_KIT_52_FWD | CGACGTAAAACGACGGCCAGTNNN NNNNNNNNNNNNTCTATTTTTCCCT TTCTCCCC | forward | 23 |
| | | IN2834_KIT_52_REV | CACACAGGAAACAGCTATGACCAT GGGGTCTATGTAAACATAATTGTT TCC | reverse | 24 |
| | KIT36 | IN2827_KIT_36_FWD | CGACGTAAAACGACGGCCAGTNNN NNNNNNNNNNNNCCATTTGACAGAA CGGGAAG | forward | 25 |
| | | IN2828_KIT_36_REV | CACACAGGAAACAGCTATGACCAT GACACGGCTTTACCTCCAATG | reverse | 26 |
| | KIT24 | IN2815_KIT_24_FWD | CGACGTAAAACGACGGCCAGTNNN NNNNNNNNNNNNTACAACGATGTGG GCAAGAC | forward | 27 |
| | | IN2816_KIT_24_REV | CACACAGGAAACAGCTATGACCAT GGACAGAGCCTAAACATCCCC | reverse | 28 |
| | KIT56 | IN3068_KIT_56_FWD | CACACAGGAAACAGCTATGACCAT GCTTCCTTATGATCACAAATGGGA | forward | 29 |
| | | IN3069_KIT_56_REV | GCGACGTAAAACGACGGCCAGTNNN NNNNNNNNNNNNGGTGACATGGAAA GCCCC | reverse | 30 |
| | KIT55 | IN2837_KIT_55_FWD | CGACGTAAAACGACGGCCAGTNNN NNNNNNNNNNNNACTCATGGTCGGA TCACAAA | forward | 31 |
| | | IN2838_KIT_55_REV | CACACAGGAAACAGCTATGACCAT GGCAGGACTGTCAAGCAGAGA | reverse | 32 |
| | KIT39 | IN2829_KIT_39_FWD | CGACGTAAAACGACGGCCAGTNNN NNNNNNNNNNNNCCTTTTCTTATGT GCTTTTAGGG | forward | 33 |
| | | IN2830_KIT_39_REV | CACACAGGAAACAGCTATGACCAT GAAATAAATGAATCACGTTTTCTT CTC | reverse | 34 |
| KIT_2 | KIT61 | IN3198_KIT_58_FWD | CGACGTAAAACGACGGCCAGTNNN NNNNNNNNNNNNAAGTACAGTGGAA GGTTGTTGAGG | forward | 35 |
| | | IN3252_KIT_61_REV | CACACAGGAAACAGCTATGACCAT GAAACTCAGCCTGTTTCTGGG | reverse | 36 |
| | KIT47 | IN2831_KIT_47_FWD | CACACAGGAAACAGCTATGACCAT GTGGCCATTTCTGTTTTCCTG | forward | 37 |

TABLE 2 -continued

KIT Primer Panel Sequences

| Panel | Primer pair ID | Primer ID | Sequence | UID primer position | SEQ ID NO: |
|---|---|---|---|---|---|
| | | IN2832_KIT_47_REV | CGACGTAAAACGACGGCCAGTNNN NNNNNNNNNNNNTGCTGCCACACAT GGAG | reverse | 38 |
| | KIT54 | IN2835_KIT_54_FWD | CGACGTAAAACGACGGCCAGTNNN NNNNNNNNNNNGCTGATTGGTTTC GTAATCGT | forward | 39 |
| | | IN2836_KIT_54_REV | CACACAGGAAACAGCTATGACCAT GTCTGGAGAGAGAACAAATAAATG G | reverse | 40 |
| | KIT12 | IN2809_KIT_12_FWD | CGACGTAAAACGACGGCCAGTNNN NNNNNNNNNNNATTATTGACTCTG TTGTGCTTCTATTACAG | forward | 41 |
| | | IN2810_KIT_12_REV | CACACAGGAAACAGCTATGACCAT GACGTCACTTTCAAACGTGTATAC AC | reverse | 42 |
| | KIT62 | IN3286_KIT_62_FWD | CGACGTAAAACGACGGCCAGTNNN NNNNNNNNNNNCTAATAGTGTATT CACAGAGACTTGGC | forward | 43 |
| | | IN3287_KIT_62_REV | CACACAGGAAACAGCTATGACCAT GTGGCTAGACCAAAATCACAAATC | reverse | 44 |

TABLE 3

KIT Exon Structure

| Exon | nt start | nt end |
|---|---|---|
| 1 | 1 | 67 |
| 2 | 68 | 337 |
| 3 | 338 | 619 |
| 4 | 620 | 756 |
| 5 | 757 | 925 |
| 6 | 926 | 1115 |
| 7 | 1116 | 1231 |
| 8 | 1232 | 1346 |
| 9 | 1347 | 1540 |
| 10 | 1541 | 1647 |
| 11 | 1648 | 1774 |
| 12 | 1774 | 1879 |
| 13 | 1880 | 1990 |
| 14 | 1991 | 2141 |
| 15 | 2142 | 2233 |
| 16 | 2234 | 2361 |
| 17 | 2362 | 2484 |
| 18 | 2485 | 2596 |
| 19 | 2597 | 2696 |
| 20 | 2697 | 2802 |
| 21 | 2803 | 2931 |

Example 2—PCR and Sequencing Conditions

UID-PCR Protocol

First, a master mix was prepared for each multiplex primer panel (UID-Mpx). To prepare the master mix, the required volumes of 5× Q5 Reaction Buffer (NEB, cat # B9027), 10 mM dNTP Mix (Life Technologies, cat #18427088), and Q5 High-Fidelity Hot Start DNA Polymerase (NEB, cat # M0493) were pipetted into a clean tube and mixed by vortexing.

To prepare UID-Mpx, primer stocks (UID-Mpx KIT_1, Sysmex Inostics, cat #6.2.032.101; UID-Mpx KIT_2, Sysmex Inostics, cat #6.2.032.102) were resuspended in fresh 1 mM EDTA, mixed by vortexing, and spun down. Primers used to amplify amplicons of panel 1 and 2 can be used in any concentration. The primer concentrations are shown in Table 4.

TABLE 4

Primer Concentrations for Panels 1 and 2

| panel 1 | primer conc. [µM] | panel 2 | primer conc. [µM] |
|---|---|---|---|
| 55 | 0.23 | 62 | 0.46 |
| 56 | 0.54 | 47 | 0.4 |
| 52 | 1.54 | 12 | 0.1 |
| 39 | 1.4 | 61 | 0.29 |
| 24 | 0.19 | 54 | 0.4 |
| 36 | 0.2 | | |

To prepare wild type reference sequence, human genomic DNA (Promega, cat # G 3041) was thawed overnight, heated to 65° C. for 10 min, mixed by vortexing, and spun down. Solutions of 0.33 ng/µL were prepared by combining the human genomic DNA and 1× TE/Glyco (SIG, cat #6.2.016.009).

PCR reactions, including no template controls (NegKo, SIG, Cat #6.2.024.001), were set up in 96-well PCR plates. PCR reactions were performed as shown in Table 5. PCR plates were stored at 2-4° C. following the completion of thermal cycling.

TABLE 5

PCR Conditions for UID-PCR

| Temperature | Time in minutes | PCR cycles | Ramp rate |
|---|---|---|---|
| 98° C. | 02:00 | 1 | |
| 98° C. | 00:20 | 10-15x | 2.5° C./s |
| 63° C. | 02:10 | | 2.5° C./s |
| 72° C. | 02:10 | | 2.5° C./s |

UID-PCR Purification Protocol

First, 35 µL of AMPure® beads (Agencourt® AMPure® XP, Beckman Coulter®, Cat # A63881) were added into each well of the 96-well plate according to plate layout, mixed by pipetted up and down 10 times, and incubated for 10 min at room temperature. The PCR plate was then placed onto the magnet (SPRI Plate 96T—Ring Super Magnet Plate; Beckman Coulter) and incubated for 5 min. The liquid was aspirated from each well of the PCR plate without disturbing the beads bound to the magnet. Then, 100 µL 70% ethanol was twice added to each well, incubated for 30 sec, and aspirated. Following the second ethanol wash, the plate was removed from the magnet and the plate allowed to air dry for 2 min at room temperature. Then, 120 µL EB buffer was slowly added to each well, mixed by pipetted up and down 20 times, and incubated for 2 min at room temperature. Then the plate was placed into the magnet and incubated for 2 min until all the beads were bound to the magnet. The supernatant was transferred to a clean 96-well plate, which was optionally stored at 2-4° C. prior to further processing. Next, the plate was placed on the magnet and incubated for 1 min. Then 5 µL of the supernatant was mixed with 99 µL of EB buffer and mixed by pipetting up and down eight times to prepare the dilution plate. Both plates were stored at 2-8° C.

WBC-PCR Protocol

To prepare WBC-Primer plates, WBC primers were resuspended in TE buffer, mixed by vortexing, and spun down. Then, to prepare WBC-Primer master plates, 50 µL WBC-forward primer (IDT; cat # IN2391) and 50 µL of 96 different reverse primers (IDT) were added to each well of a 96-well plate. To prepare a WBC-sub plate, each well of the mater place was diluted 1:10 with TE-buffer into a new 96-well plate.

UID-Mpx specific master mixes were prepared and pipetted into the PCR plate according to the plate layout. Then, 2.5 µL WBC primer and the template were added to the appropriate wells of the PCR plate and mixed by pipetted up and down three times. The input amount for the amplification of UID-assigned amplicons may vary between 0.1% and 1% of purified UID-assigned PCR products. PCR reactions were performed as shown in Table 6. PCR plates were stored at 2-8° C. following the completion of thermal cycling.

TABLE 6

PCR Conditions for WBC-PCR

| Temperature | Time in minutes | PCR cycles | Ramp rate |
|---|---|---|---|
| 98° C. | 02:00 | 1 | |
| 98° C. | 00:20 | 16-21x | 2.5° C./s |
| 65° C. | 02:10 | | 2.5° C./s |
| 72° C. | 02:10 | | 2.5° C./s |

WBC-PCR Purification

Each PCR product amplified with one UID-Mpx may not be mixed with PCR-products of another UID-Mpx. They must be purified separately.

For the first round of purification, all of the liquid from the wells of a single UID-Mpx were collected and mixed in a tube while avoiding bubble formation. AMPure beads (Agencourt AMPure XP, Beckman Coulter, Cat # A63881) were added to the tube, mixed well by vortexing for 10 s, and incubated at room temperature for 5 min. Then the tube was placed on a Dyna-Mag-15 and incubated for 5 min, after which the supernatant was removed and discarded. The inside wall of the tube was twice rinsed with 70% ethanol and the supernatant removed and discarded after a 30 sec incubation. After removing any residual ethanol, the tube was removed from the magnet and allowed to air dry for 2 min at room temperature.

Next, 70 µL EB buffer (Qiagen) was added to the tube and the beads were resuspended by vortexing. The bead suspension was then spun down for 20 sec at 200 rcf. The bead suspension was then transferred to a clean tube, incubated at room temperature for 1 min, and placed on the Dyna-Mag-15 for 1 min to bind all beads to the magnet-side of the tube. Eighty microliters of the eluate were moved to a clean tube. This process was repeated twice for a total of 160 µL eluate collected.

For the second round of purification, 40 µL 5× Phusion GC Buffer (Thermo, Cat # F-519) was added to the eluate, mixed by vortexing, and spun down. AMPure beads (220 µL) were added to the eluate, vortexed, and spun down. Following a 5 min incubation at room temperature, the tube was placed on the Dyna-Mag-2 and incubated for 2 min. The supernatant was removed and 500 µL 70% ethanol was added. Following a 30 sec incubation at room temperature, the supernatant was removed and 500 µL 70% ethanol was added. During a 30 sec incubation at room temperature, the tube was turned around the vertical axis by 180° for 5 sec to let the beads fly through the ethanol. The supernatant was completely aspirated, the tube removed from the magnet, and the beads allowed to air dry for 2 min at room temperature.

Next, 40 µL EB buffer (Qiagen) was added to the tube and the beads were resuspended by vortexing. The bead suspension was then spun down and the tube incubated for 1 min at room temperature. The tube was then placed on the Dyna-Mag-2 and incubated for 1 min until all the beads were bound to the magnet side of the tube. Then, 40 µL of the supernatant was carefully transferred into a clean tube without disturbing the bead pellet. This process was repeated twice for a total of 80 µL supernatant collected.

For the third round of purification, 20 µL 5× Phusion GC Buffer (Thermo, Cat # F-519) was added to the supernatant, mixed by vortexing, and spun down. AMPure beads (100 µL) were added to the supernatant, vortexed, and spun down. Following a 5 min incubation at room temperature, the tube was placed on the Dyna-Mag-2 and incubated for 2 min at room temperature. The supernatant was removed and 500 µL 70% ethanol was added. Following a 30 sec incubation at room temperature, the supernatant was removed and 500 µL 70% ethanol was added. During a 30 sec incubation at room temperature, the tube was turned around the vertical axis by 180° for 5 sec to let the beads fly through the ethanol. The supernatant was completely aspirated, the tube removed from the magnet, and the beads allowed to air dry for 2 min at room temperature.

Next, 10 µL EB buffer (Qiagen) was added to the tube and the beads were resuspended by vortexing. The bead suspension was then spun down and the tube incubated for 1 min at room temperature. The tube was then placed on the Dyna-Mag-2 and incubated for 1 min until all the beads were bound to the magnet side of the tube. Then, all of the supernatant was carefully transferred into a clean tube without disturbing the bead pellet. The supernatant was stored at −20° C.

Quantification of WBC-PCR Using Bioanalyzer

Distilled water (360 μL) was added to the cleaning chip and placed into the Bioanalyzer (Bioanalyzer 2100, Agilent) for 10 sec. Following removal of the cleaning chip, the electrodes were allowed to dry for 1 min. Labchips were prepared according to the manufacturer's instructions. Data analysis was performed either based on regions or by manual integration depending on whether the base line was directly on top of the signal line.

Sequencing Protocol

To prepare 1 nM PhiX control, the stock of PhiX control Kit v3 (Illumina; cat # FC-110-3001) was diluted 1:10 in EB buffer by adding 10 mL of PhiX to 90 μL EB buffer. First, 1 μL 1 nM PhiX (SIG, cat # FC-110-3001) was added to 10 μL 0.1 M NaOH, mixed by vortexing, and spun down. The mixture was incubated for 5 min at room temperature to denature the dsDNA into ssDNA. Then, 980 μL of Buffer HT1 was added and mixed by vortexing. Next, 400 μL Buffer HT1 was added to a clean tube, mixed with 600 μL of the PhiX mixture by vortexing, and stored at 2-8° C.

To prepare sequencing primers, primer stocks were resuspended in 1 mM EDTA to achieve a concentration of 100 mM. After mixing the reagents in the cartridge (MiSeq® v3 Reagent Kit, Illumina, cat # MS-102-3001) by inverting the cartridge 10 times, the liquid in positions 12 and 13 were removed and placed into individual clean tubes. These tubes were spun down and then 7 μL of sequencing primers 12 (SIG, cat #6.2.032.012) and 13 (SIG, cat #6.2.032.013) were added to each tube, respectively. The tubes were then vortexed and spun down, after which the primer solutions were added by to their respective positions on the cartridge. Finally, 600 μL of the final PhiX mixture was added to the "sample" position on the cartridge.

On the MiSeq Benchtop Sequencer (Illumina), the flowcell was cleaned using ultrapure water and lint-free tissue. Then the cartridge was inserted into the flowcell and the sequencing run performed.

Example 3—Safe-Sequencing of KIT UIDs Vs. Conventional NGS of KIT

Provided here is the comparison of the use of the present KIT primer sets in Safe-Sequencing versus NGS. The same data was analyzed from one experiment with and without UIDs. This allows for an unbiased comparison of the use of the KIT primer sets in the context of Safe-Sequencing and in the context of conventional NGS.

UID-Primers were used to amplify amplicons of interest in a multiplex PCR using wild-type genomic human DNA. Primers used here are shown in FIGS. 3 to 6.

UID-PCR products were purified to remove residual primers, reagents, and salts. The PCR-products were also diluted to limit the input material for WBC-PCR. WBC-PCR was used to amplify purified UID-PCR products, giving rise to UID families. Each well of a 96-well PCR plate was assigned a well-specific 6-mer sequence (well barcode) to identify samples and subsample replicate wells. In addition, Illumina-adaptor sequences were added during this PCR.

WBC-PCR products were purified using AMPure magnetic beads that bind DNA. In a process of three consecutive rounds of purification, the AMPure-concentration was decreased to focus purification on the desired PCR products in the size range of 180-250 bp.

To determine the DNA input amount for sequencing, purified WBC-PCR products were quantified using the Bioanalyzer capillary electrophoresis system. WBC-PCR products were diluted, denatured, and subjected to sequencing by synthesis using M13 primers. Data-analysis for Safe-Sequencing was performed to count UID families, UID family sizes, and identify supermutants, which are considered background in the case of wild-type genomic human DNA input. Data analysis without UIDs (Conventional Sequencing) was performed by counting unique reads and calculating the background.

Figure 3:
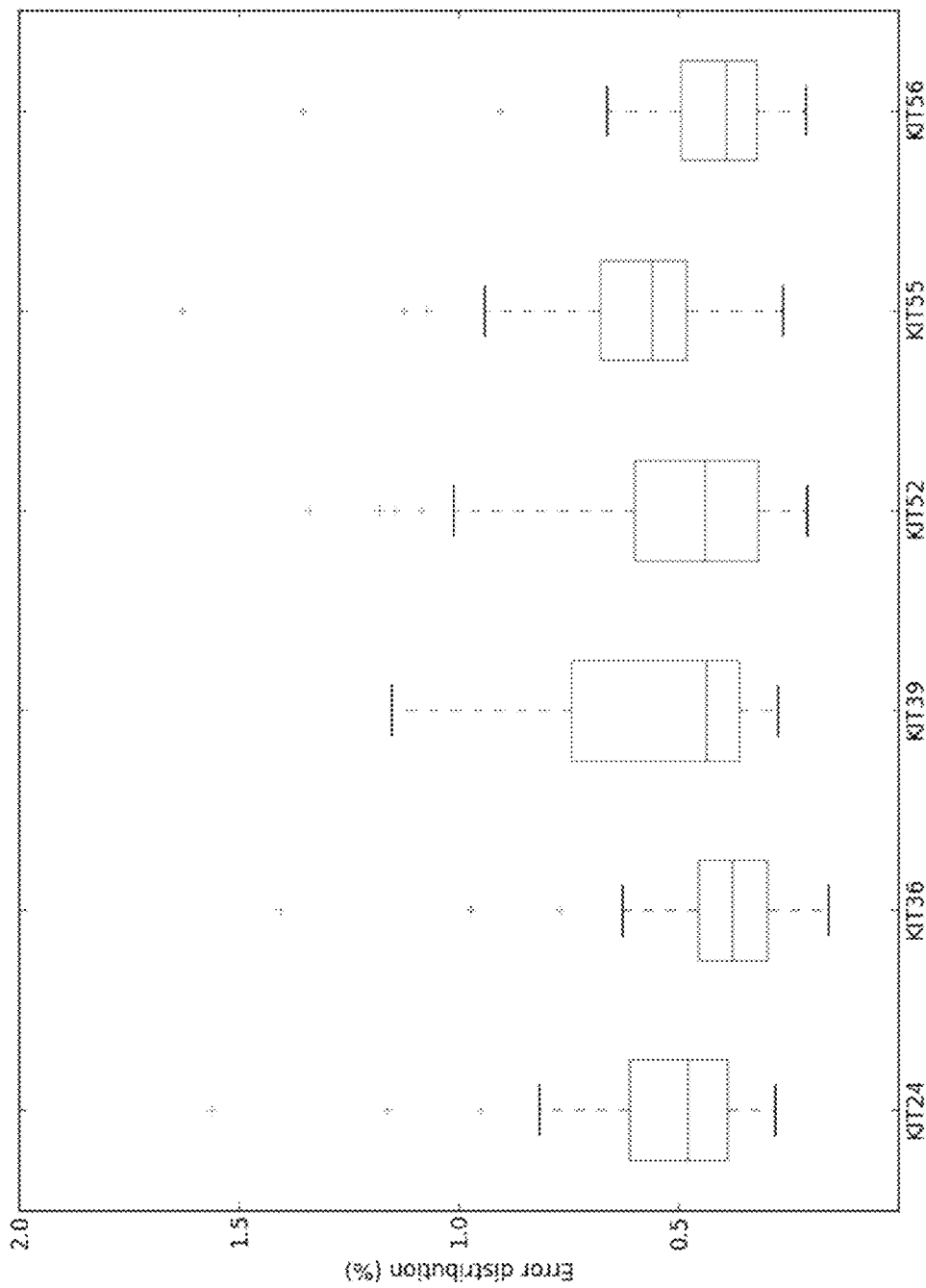
FIG. 3. Box plot showing percent error distribution using conventional sequencing with KIT primer panel 1.
Figure 4:
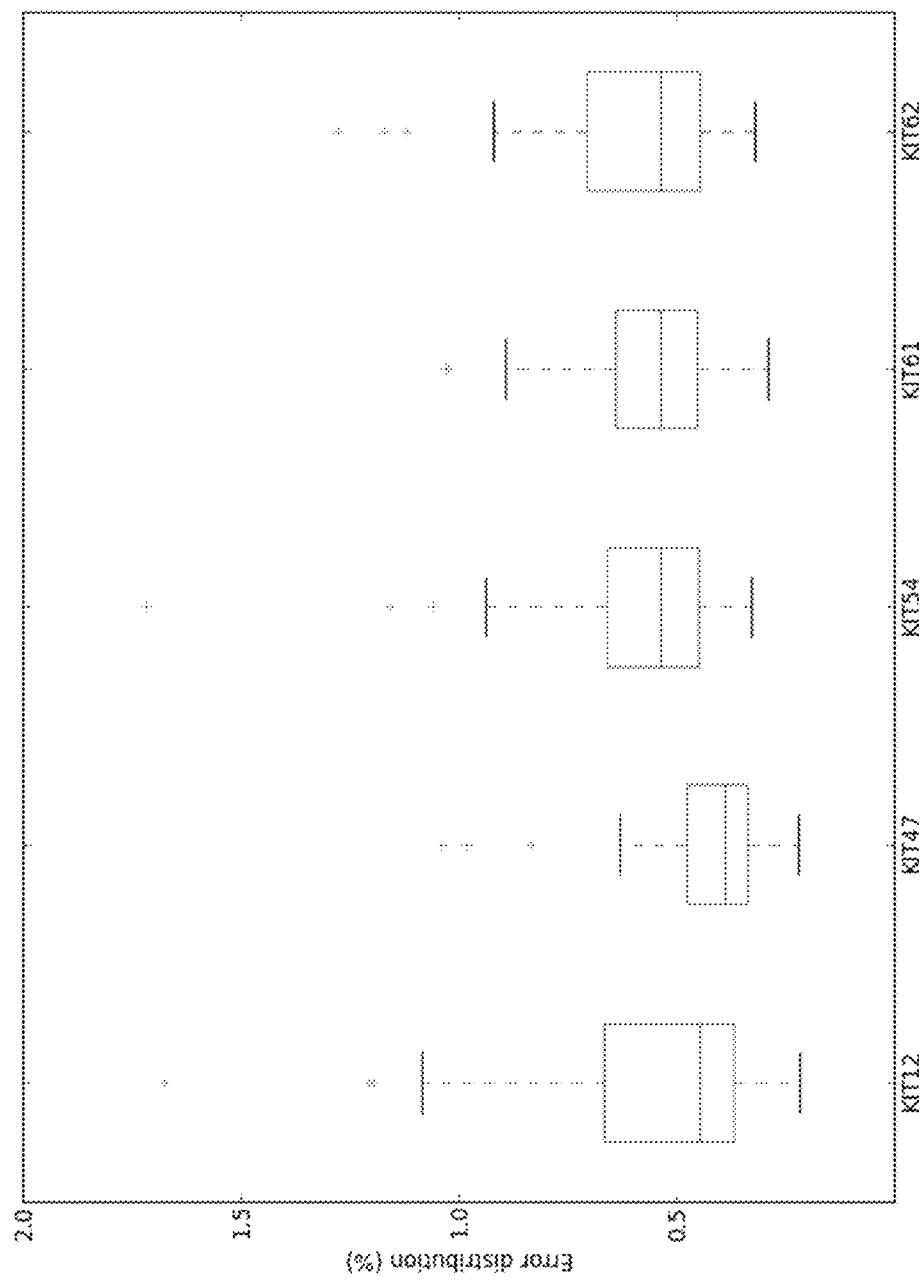
FIG. 4. Box plot showing percent error distribution using conventional sequencing with KIT primer panel 2.
Figure 5:
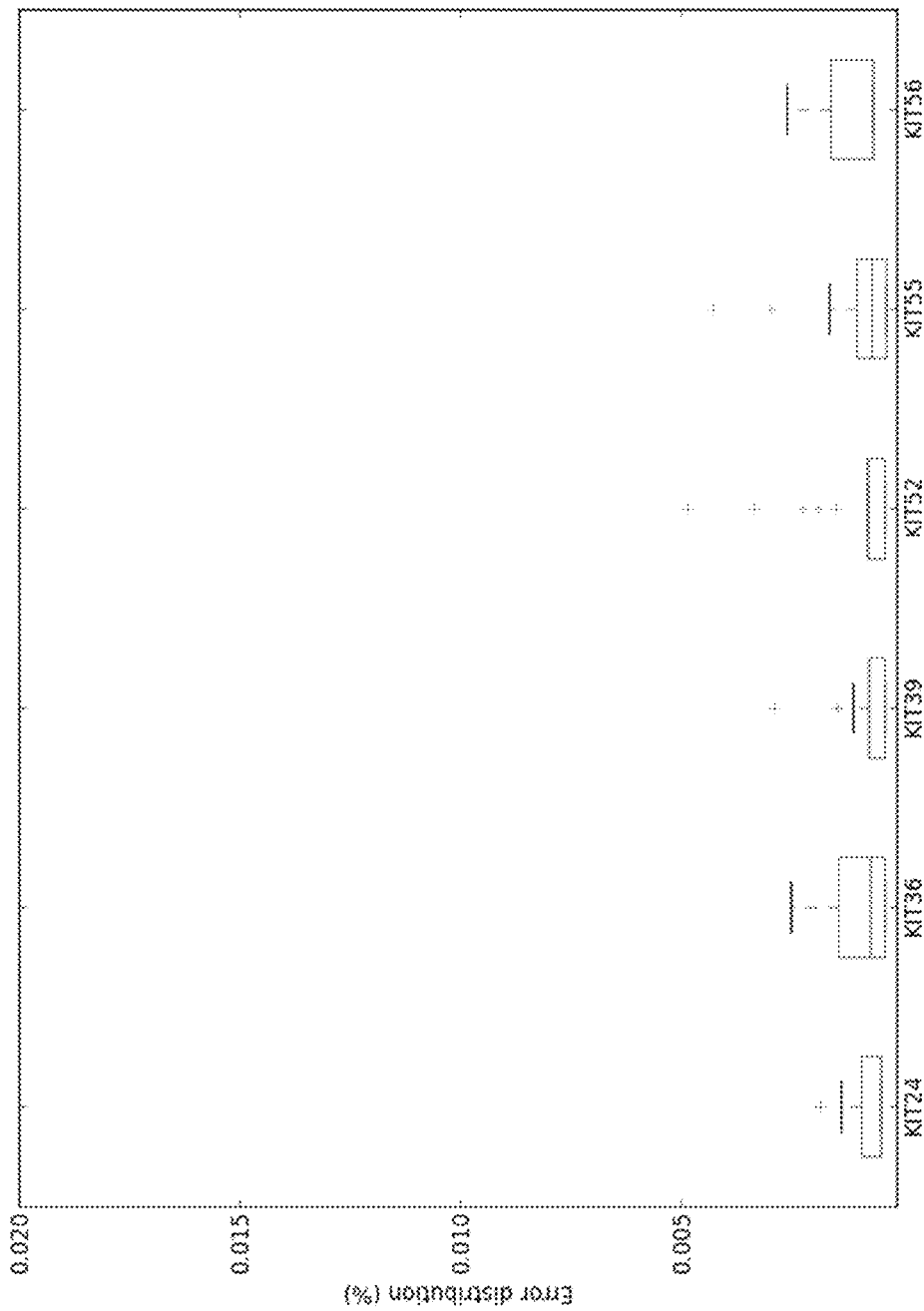
FIG. 5. Box plot showing percent error distribution using Safe-Sequencing with KIT primer panel 1.
Figure 6:
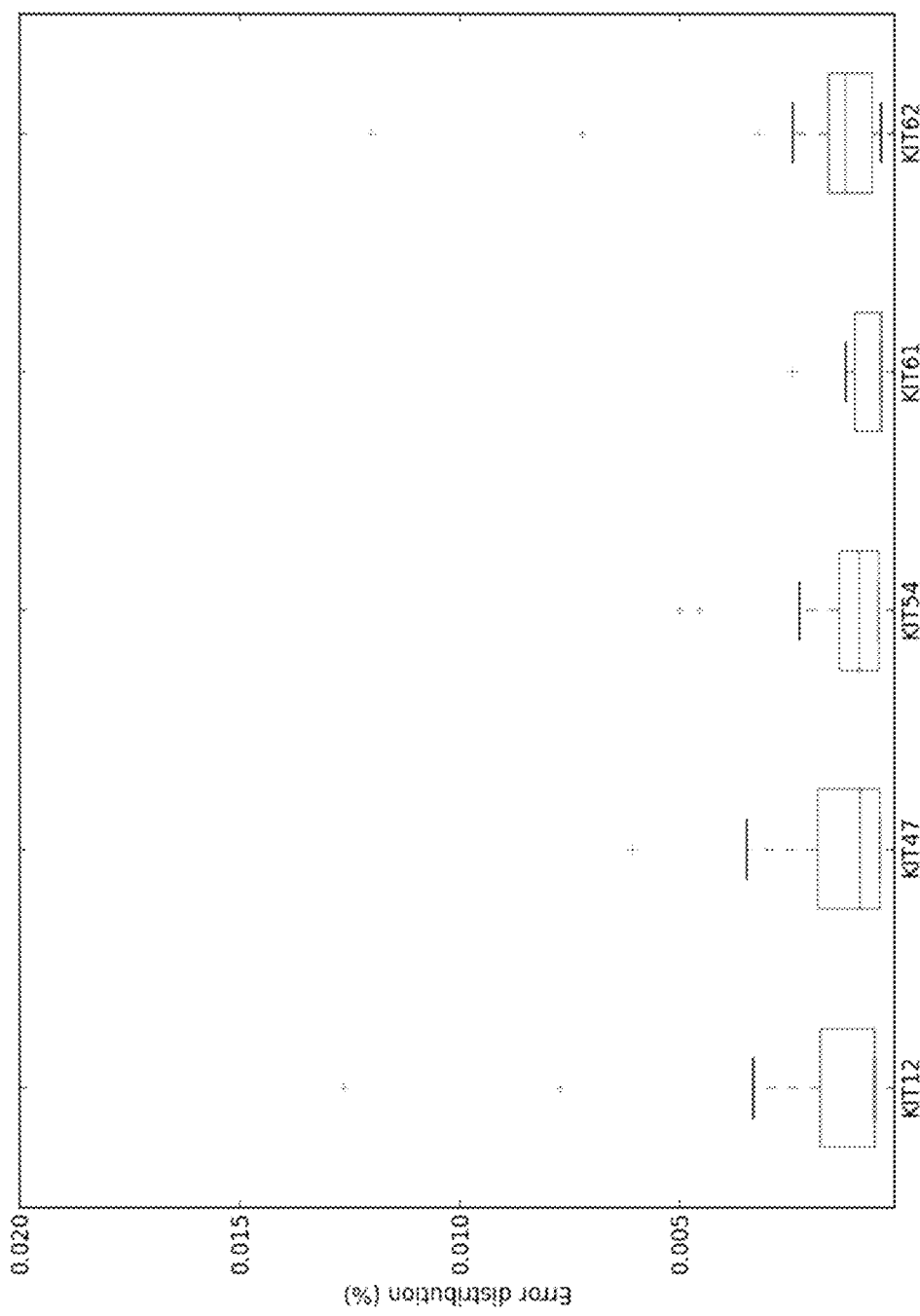
FIG. 6. Box plot showing percent error distribution using Safe-Sequencing with KIT primer panel 2.

Data analysis comparing the analysis using (Safe-Sequencing; FIGS. 5-6) and not using (Conventional Sequencing; FIGS. 3-4) the UIDs showed that the UIDs allowed for a ~500-fold decrease in background (i.e., polymerase errors) in comparison to analysis without UIDs (FIGS. 3-6). This allows for 500-fold more reliability and sensitivity by using the UIDs.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A reagent kit for detecting mutation of a KIT gene in a specimen comprising DNA, the kit comprising a first reagent and a second reagent, the first reagent comprising a mixture of primer sets of: (i) a forward primer comprising the sequence of SEQ ID NO: 31 and a reverse primer comprising the sequence of SEQ ID NO: 32; (ii) a forward primer comprising the sequence of SEQ ID NO: 29 and a reverse primer comprising the sequence of SEQ ID NO: 30; (iii) a forward primer comprising the sequence of SEQ ID NO: 23 and a reverse primer comprising the sequence of SEQ ID NO: 24; (iv) a forward primer comprising the sequence of SEQ ID NO: 33 and a reverse primer comprising the sequence of SEQ ID NO: 34; (v) a forward primer comprising the sequence of SEQ ID NO: 27 and a reverse primer comprising the sequence of SEQ ID NO: 28; and/or (vi) a forward primer comprising the sequence of SEQ ID NO: 25 and a reverse primer comprising the sequence of SEQ ID NO: 26; and the second reagent comprising one or more primer sets selected from (vii) a forward primer comprising the sequence of SEQ ID NO: 41 and a reverse primer comprising the sequence of SEQ ID NO: 42; (vii) a forward primer comprising the sequence of SEQ ID NO: 37 and a reverse primer comprising the sequence of SEQ ID NO: 38; (ix) a forward primer comprising the sequence of SEQ ID NO: 39 and a reverse primer comprising the sequence of SEQ ID NO: 40; (x) a forward primer comprising the sequence of SEQ ID NO: 35 and a reverse primer comprising the sequence of SEQ ID NO: 36; and/or (xi) a forward primer comprising the sequence of SEQ ID NO: 43 and a reverse primer comprising the sequence of SEQ ID NO: 44.

2. A method for detecting a mutation of a KIT gene using the reagent kit of claim 1, comprising: (a) amplifying KIT gene DNA using the first reagent; (b) amplifying KIT gene DNA using the second reagent; and (c) detecting the mutation of the KIT gene by obtaining sequence information on the amplified DNA.

3. The method of claim 2, wherein the method is further defined as a method of detecting cancer.

4. The method of claim 2, wherein the method is further defined as a method of detecting resistance or susceptibility to drugs targeting KIT.

5. The method of claim 4, wherein the drug is imatinib.

6. A method of treating a subject comprising administering an effective amount of a KIT targeting drug to a subject determined to be susceptible to the drug in accordance with claim 4.

7. The method according to claim 2, wherein the amplification using the first reagent is performed by multiplex PCR; and the amplification using the second reagent is performed by multiplex PCR.

8. The reagent kit of claim 1, the first reagent comprising a mixture of primer sets of: (i) a forward primer comprising the sequence of SEQ ID NO: 31 and a reverse primer comprising the sequence of SEQ ID NO: 32; (ii) a forward primer comprising the sequence of SEQ ID NO: 29 and a reverse primer comprising the sequence of SEQ ID NO: 30; (iii) a forward primer comprising the sequence of SEQ ID NO: 23 and a reverse primer comprising the sequence of SEQ ID NO: 24; (iv) a forward primer comprising the sequence of SEQ ID NO: 33 and a reverse primer comprising the sequence of SEQ ID NO: 34; (v) a forward primer comprising the sequence of SEQ ID NO: 27 and a reverse primer comprising the sequence of SEQ ID NO: 28; and (vi) a forward primer comprising the sequence of SEQ ID NO: 25 and a reverse primer comprising the sequence of SEQ ID NO: 26; and the second reagent comprising one or more primer sets selected from (vii) a forward primer comprising the sequence of SEQ ID NO: 41 and a reverse primer comprising the sequence of SEQ ID NO: 42; (vii) a forward primer comprising the sequence of SEQ ID NO: 37 and a reverse primer comprising the sequence of SEQ ID NO: 38; (ix) a forward primer comprising the sequence of SEQ ID NO: 39 and a reverse primer comprising the sequence of SEQ ID NO: 40; (x) a forward primer comprising the sequence of SEQ ID NO: 35 and a reverse primer comprising the sequence of SEQ ID NO: 36; and/or (xi) a forward primer comprising the sequence of SEQ ID NO: 43 and a reverse primer comprising the sequence of SEQ ID NO: 44.

9. The reagent kit of claim 1, the first reagent comprising a mixture of primer sets of: (i) a forward primer comprising the sequence of SEQ ID NO: 31 and a reverse primer comprising the sequence of SEQ ID NO: 32; (ii) a forward primer comprising the sequence of SEQ ID NO: 29 and a reverse primer comprising the sequence of SEQ ID NO: 30; (iii) a forward primer comprising the sequence of SEQ ID NO: 23 and a reverse primer comprising the sequence of SEQ ID NO: 24; (iv) a forward primer comprising the sequence of SEQ ID NO: 33 and a reverse primer comprising the sequence of SEQ ID NO: 34; (v) a forward primer comprising the sequence of SEQ ID NO: 27 and a reverse primer comprising the sequence of SEQ ID NO: 28; and/or (vi) a forward primer comprising the sequence of SEQ ID NO: 25 and a reverse primer comprising the sequence of SEQ ID NO: 26; and the second reagent comprising the primer sets (vii) a forward primer comprising the sequence of SEQ ID NO: 41 and a reverse primer comprising the sequence of SEQ ID NO: 42; (vii) a forward primer comprising the sequence of SEQ ID NO: 37 and a reverse primer comprising the sequence of SEQ ID NO: 38; (ix) a forward primer comprising the sequence of SEQ ID NO: 39 and a reverse primer comprising the sequence of SEQ ID NO: 40; (x) a forward primer comprising the sequence of SEQ ID NO: 35 and a reverse primer comprising the sequence of SEQ ID NO: 36; and (xi) a forward primer comprising the sequence of SEQ ID NO: 43 and a reverse primer comprising the sequence of SEQ ID NO: 44.

10. The reagent kit of claim 1, the first reagent comprising a mixture of primer sets of: (i) a forward primer comprising the sequence of SEQ ID NO: 31 and a reverse primer comprising the sequence of SEQ ID NO: 32; (ii) a forward primer comprising the sequence of SEQ ID NO: 29 and a reverse primer comprising the sequence of SEQ ID NO: 30; (iii) a forward primer comprising the sequence of SEQ ID NO: 23 and a reverse primer comprising the sequence of SEQ ID NO: 24; (iv) a forward primer comprising the sequence of SEQ ID NO: 33 and a reverse primer comprising the sequence of SEQ ID NO: 34; (v) a forward primer comprising the sequence of SEQ ID NO: 27 and a reverse primer comprising the sequence of SEQ ID NO: 28; and (vi) a forward primer comprising the sequence of SEQ ID NO: 25 and a reverse primer comprising the sequence of SEQ ID NO: 26; and the second reagent comprising the primer sets (vii) a forward primer comprising the sequence of SEQ ID NO: 41 and a reverse primer comprising the sequence of SEQ ID NO: 42; (vii) a forward primer comprising the sequence of SEQ ID NO: 37 and a reverse primer comprising the sequence of SEQ ID NO: 38; (ix) a forward primer comprising the sequence of SEQ ID NO: 39 and a reverse primer comprising the sequence of SEQ ID NO: 40; (x) a forward primer comprising the sequence of SEQ ID NO: 35 and a reverse primer comprising the sequence of SEQ ID NO: 36; and (xi) a forward primer comprising the sequence of SEQ ID NO: 43 and a reverse primer comprising the sequence of SEQ ID NO: 44.

* * * * *

SEQUENCE LISTING

<160> NUMBER OF SEQ ID NOS: 49

<210> SEQ ID NO 1
<211> LENGTH: 30
<212> TYPE: DNA
<213> ORGANISM: Artificial sequence
<220> FEATURE:
<223> OTHER INFORMATION: Synthetic primer

<400> SEQUENCE: 1
attattgact ctgttgtgct tctattacag                    30

```
<210> SEQ ID NO 2
<211> LENGTH: 25
<212> TYPE: DNA
<213> ORGANISM: Artificial sequence
<220> FEATURE:
<223> OTHER INFORMATION: Synthetic primer

<400> SEQUENCE: 2
acgtcacttt caaacgtgta tacac                                              25

<210> SEQ ID NO 3
<211> LENGTH: 20
<212> TYPE: DNA
<213> ORGANISM: Artificial sequence
<220> FEATURE:
<223> OTHER INFORMATION: Synthetic primer

<400> SEQUENCE: 3
tacaacgatg tgggcaagac                                                    20

<210> SEQ ID NO 4
<211> LENGTH: 20
<212> TYPE: DNA
<213> ORGANISM: Artificial sequence
<220> FEATURE:
<223> OTHER INFORMATION: Synthetic primer

<400> SEQUENCE: 4
gacagagcct aaacatcccc                                                    20

<210> SEQ ID NO 5
<211> LENGTH: 20
<212> TYPE: DNA
<213> ORGANISM: Artificial sequence
<220> FEATURE:
<223> OTHER INFORMATION: Synthetic primer

<400> SEQUENCE: 5
ccatttgaca gaacgggaag                                                    20

<210> SEQ ID NO 6
<211> LENGTH: 20
<212> TYPE: DNA
<213> ORGANISM: Artificial sequence
<220> FEATURE:
<223> OTHER INFORMATION: Synthetic primer

<400> SEQUENCE: 6
acacggcttt acctccaatg                                                    20

<210> SEQ ID NO 7
<211> LENGTH: 23
<212> TYPE: DNA
<213> ORGANISM: Artificial sequence
<220> FEATURE:
<223> OTHER INFORMATION: Synthetic primer

<400> SEQUENCE: 7
ccttttctta tgtgctttta ggg                                                23

<210> SEQ ID NO 8
<211> LENGTH: 26
<212> TYPE: DNA
<213> ORGANISM: Artificial sequence
<220> FEATURE:
<223> OTHER INFORMATION: Synthetic primer
```

```
<400> SEQUENCE: 8
aaataaatga atcacgtttt cttctc                                         26

<210> SEQ ID NO 9
<211> LENGTH: 20
<212> TYPE: DNA
<213> ORGANISM: Artificial sequence
<220> FEATURE:
<223> OTHER INFORMATION: Synthetic primer

<400> SEQUENCE: 9
tggccatttc tgttttcctg                                                20

<210> SEQ ID NO 10
<211> LENGTH: 18
<212> TYPE: DNA
<213> ORGANISM: Artificial sequence
<220> FEATURE:
<223> OTHER INFORMATION: Synthetic primer

<400> SEQUENCE: 10
tgctgccaca cattggag                                                  18

<210> SEQ ID NO 11
<211> LENGTH: 21
<212> TYPE: DNA
<213> ORGANISM: Artificial sequence
<220> FEATURE:
<223> OTHER INFORMATION: Synthetic primer

<400> SEQUENCE: 11 tctattttc cctttctccc c                                               21

<210> SEQ ID NO 12
<211> LENGTH: 26
<212> TYPE: DNA
<213> ORGANISM: Artificial sequence
<220> FEATURE:
<223> OTHER INFORMATION: Synthetic primer

<400> SEQUENCE: 12
gggtctatgt aaacataatt gtttcc                                         26

<210> SEQ ID NO 13
<211> LENGTH: 21
<212> TYPE: DNA
<213> ORGANISM: Artificial sequence
<220> FEATURE:
<223> OTHER INFORMATION: Synthetic primer

<400> SEQUENCE: 13
gctgattggt ttcgtaatcg t                                              21

<210> SEQ ID NO 14
<211> LENGTH: 24
<212> TYPE: DNA
<213> ORGANISM: Artificial sequence
<220> FEATURE:
<223> OTHER INFORMATION: Synthetic primer

<400> SEQUENCE: 14
tctggagaga gaacaaataa atgg                                           24

<210> SEQ ID NO 15
```

```
<211> LENGTH: 20
<212> TYPE: DNA
<213> ORGANISM: Artificial sequence
<220> FEATURE:
<223> OTHER INFORMATION: Synthetic primer

<400> SEQUENCE: 15
actcatggtc ggatcacaaa                                                   20

<210> SEQ ID NO 16
<211> LENGTH: 20
<212> TYPE: DNA
<213> ORGANISM: Artificial sequence
<220> FEATURE:
<223> OTHER INFORMATION: Synthetic primer

<400> SEQUENCE: 16
gcaggactgt caagcagaga                                                   20

<210> SEQ ID NO 17
<211> LENGTH: 24
<212> TYPE: DNA
<213> ORGANISM: Artificial sequence
<220> FEATURE:
<223> OTHER INFORMATION: Synthetic primer

<400> SEQUENCE: 17
cttccttatg atcacaaatg ggag                                              24

<210> SEQ ID NO 18
<211> LENGTH: 18
<212> TYPE: DNA
<213> ORGANISM: Artificial sequence
<220> FEATURE:
<223> OTHER INFORMATION: Synthetic primer

<400> SEQUENCE: 18
ggtgacatgg aaagcccc                                                     18

<210> SEQ ID NO 19
<211> LENGTH: 24
<212> TYPE: DNA
<213> ORGANISM: Artificial sequence
<220> FEATURE:
<223> OTHER INFORMATION: Synthetic primer

<400> SEQUENCE: 19
aagtacagtg gaaggttgtt gagg                                              24

<210> SEQ ID NO 20
<211> LENGTH: 20
<212> TYPE: DNA
<213> ORGANISM: Artificial sequence
<220> FEATURE:
<223> OTHER INFORMATION: Synthetic primer

<400> SEQUENCE: 20
aaactcagcc tgtttctggg                                                   20

<210> SEQ ID NO 21
<211> LENGTH: 27
<212> TYPE: DNA
<213> ORGANISM: Artificial sequence
<220> FEATURE:
<223> OTHER INFORMATION: Synthetic primer

<400> SEQUENCE: 21
```
ctaatagtgt attcacagag acttggc					27

<210> SEQ ID NO 22
<211> LENGTH: 23
<212> TYPE: DNA
<213> ORGANISM: Artificial sequence
<220> FEATURE:
<223> OTHER INFORMATION: Synthetic primer

<400> SEQUENCE: 22
tggctagacc aaaatcacaa atc					23

<210> SEQ ID NO 23
<211> LENGTH: 56
<212> TYPE: DNA
<213> ORGANISM: Artificial sequence
<220> FEATURE:
<223> OTHER INFORMATION: Synthetic primer panel
<220> FEATURE:
<221> NAME/KEY: misc_feature
<222> LOCATION: (22)..(35)
<223> OTHER INFORMATION: n is a, c, g, or t

<400> SEQUENCE: 23
cgacgtaaaa cgacggccag tnnnnnnnnn nnnnntctat ttttcccttt ctcccc					56

<210> SEQ ID NO 24
<211> LENGTH: 51
<212> TYPE: DNA
<213> ORGANISM: Artificial sequence
<220> FEATURE:
<223> OTHER INFORMATION: Synthetic primer panel

<400> SEQUENCE: 24
cacacaggaa acagctatga ccatggggtc tatgtaaaca taattgtttc c					51

<210> SEQ ID NO 25
<211> LENGTH: 55
<212> TYPE: DNA
<213> ORGANISM: Artificial sequence
<220> FEATURE:
<223> OTHER INFORMATION: Synthetic primer panel
<220> FEATURE:
<221> NAME/KEY: misc_feature
<222> LOCATION: (22)..(35)
<223> OTHER INFORMATION: n is a, c, g, or t

<400> SEQUENCE: 25
cgacgtaaaa cgacggccag tnnnnnnnnn nnnnnccatt tgacagaacg ggaag					55

<210> SEQ ID NO 26
<211> LENGTH: 45
<212> TYPE: DNA
<213> ORGANISM: Artificial sequence
<220> FEATURE:
<223> OTHER INFORMATION: Synthetic primer panel

<400> SEQUENCE: 26
cacacaggaa acagctatga ccatgacacg gctttacctc caatg					45

<210> SEQ ID NO 27
<211> LENGTH: 55
<212> TYPE: DNA
<213> ORGANISM: Artificial sequence
<220> FEATURE:
<223> OTHER INFORMATION: Synthetic primer panel
<220> FEATURE:

```
<221> NAME/KEY: misc_feature
<222> LOCATION: (22)..(35)
<223> OTHER INFORMATION: n is a, c, g, or t

<400> SEQUENCE: 27
cgacgtaaaa cgacggccag tnnnnnnnnn nnnnntacaa cgatgtgggc aagac      55

<210> SEQ ID NO 28
<211> LENGTH: 45
<212> TYPE: DNA
<213> ORGANISM: Artificial sequence
<220> FEATURE:
<223> OTHER INFORMATION: Synthetic primer panel

<400> SEQUENCE: 28
cacacaggaa acagctatga ccatggacag agcctaaaca tcccc      45

<210> SEQ ID NO 29
<211> LENGTH: 49
<212> TYPE: DNA
<213> ORGANISM: Artificial sequence
<220> FEATURE:
<223> OTHER INFORMATION: Synthetic primer panel

<400> SEQUENCE: 29
cacacaggaa acagctatga ccatgcttcc ttatgatcac aaatgggag      49

<210> SEQ ID NO 30
<211> LENGTH: 53
<212> TYPE: DNA
<213> ORGANISM: Artificial sequence
<220> FEATURE:
<223> OTHER INFORMATION: Synthetic primer panel
<220> FEATURE:
<221> NAME/KEY: misc_feature
<222> LOCATION: (22)..(35)
<223> OTHER INFORMATION: n is a, c, g, or t

<400> SEQUENCE: 30
cgacgtaaaa cgacggccag tnnnnnnnnn nnnnggtga catggaaagc ccc      53

<210> SEQ ID NO 31
<211> LENGTH: 55
<212> TYPE: DNA
<213> ORGANISM: Artificial sequence
<220> FEATURE:
<223> OTHER INFORMATION: Synthetic primer panel
<220> FEATURE:
<221> NAME/KEY: misc_feature
<222> LOCATION: (22)..(35)
<223> OTHER INFORMATION: n is a, c, g, or t

<400> SEQUENCE: 31
cgacgtaaaa cgacggccag tnnnnnnnnn nnnnnactca tggtcggatc acaaa      55

<210> SEQ ID NO 32
<211> LENGTH: 45
<212> TYPE: DNA
<213> ORGANISM: Artificial sequence
<220> FEATURE:
<223> OTHER INFORMATION: Synthetic primer panel

<400> SEQUENCE: 32
cacacaggaa acagctatga ccatggcagg actgtcaagc agaga      45

<210> SEQ ID NO 33
<211> LENGTH: 58
```

```
<212> TYPE: DNA
<213> ORGANISM: Artificial sequence
<220> FEATURE:
<223> OTHER INFORMATION: Synthetic primer panel
<220> FEATURE:
<221> NAME/KEY: misc_feature
<222> LOCATION: (22)..(35)
<223> OTHER INFORMATION: n is a, c, g, or t

<400> SEQUENCE: 33
cgacgtaaaa cgacggccag tnnnnnnnnn nnnnncctttt tcttatgtgc ttttaggg      58

<210> SEQ ID NO 34
<211> LENGTH: 51
<212> TYPE: DNA
<213> ORGANISM: Artificial sequence
<220> FEATURE:
<223> OTHER INFORMATION: Synthetic primer panel

<400> SEQUENCE: 34
cacacaggaa acagctatga ccatgaaata aatgaatcac gttttcttct c             51

<210> SEQ ID NO 35
<211> LENGTH: 59
<212> TYPE: DNA
<213> ORGANISM: Artificial sequence
<220> FEATURE:
<223> OTHER INFORMATION: Synthetic primer panel
<220> FEATURE:
<221> NAME/KEY: misc_feature
<222> LOCATION: (22)..(35)
<223> OTHER INFORMATION: n is a, c, g, or t

<400> SEQUENCE: 35
cgacgtaaaa cgacggccag tnnnnnnnnn nnnnnaagta cagtggaagg ttgttgagg     59

<210> SEQ ID NO 36
<211> LENGTH: 45
<212> TYPE: DNA
<213> ORGANISM: Artificial sequence
<220> FEATURE:
<223> OTHER INFORMATION: Synthetic primer panel

<400> SEQUENCE: 36
cacacaggaa acagctatga ccatgaaact cagcctgttt ctggg                    45

<210> SEQ ID NO 37
<211> LENGTH: 45
<212> TYPE: DNA
<213> ORGANISM: Artificial sequence
<220> FEATURE:
<223> OTHER INFORMATION: Synthetic primer panel

<400> SEQUENCE: 37
cacacaggaa acagctatga ccatgtggcc atttctgttt tcctg                    45

<210> SEQ ID NO 38
<211> LENGTH: 53
<212> TYPE: DNA
<213> ORGANISM: Artificial sequence
<220> FEATURE:
<223> OTHER INFORMATION: Synthetic primer panel
<220> FEATURE:
<221> NAME/KEY: misc_feature
<222> LOCATION: (22)..(35)
<223> OTHER INFORMATION: n is a, c, g, or t

<400> SEQUENCE: 38
```

```
cgacgtaaaa cgacggccag tnnnnnnnnn nnnnntgctg ccacacattg gag            53
```

<210> SEQ ID NO 39
<211> LENGTH: 56
<212> TYPE: DNA
<213> ORGANISM: Artificial sequence
<220> FEATURE:
<223> OTHER INFORMATION: Synthetic primer panel
<220> FEATURE:
<221> NAME/KEY: misc_feature
<222> LOCATION: (22)..(35)
<223> OTHER INFORMATION: n is a, c, g, or t

<400> SEQUENCE: 39

```
cgacgtaaaa cgacggccag tnnnnnnnnn nnnnngctga ttggtttcgt aatcgt         56
```

<210> SEQ ID NO 40
<211> LENGTH: 49
<212> TYPE: DNA
<213> ORGANISM: Artificial sequence
<220> FEATURE:
<223> OTHER INFORMATION: Synthetic primer panel

<400> SEQUENCE: 40

```
cacacaggaa acagctatga ccatgtctgg agagagaaca aataaatgg                 49
```

<210> SEQ ID NO 41
<211> LENGTH: 65
<212> TYPE: DNA
<213> ORGANISM: Artificial sequence
<220> FEATURE:
<223> OTHER INFORMATION: Synthetic primer panel
<220> FEATURE:
<221> NAME/KEY: misc_feature
<222> LOCATION: (22)..(35)
<223> OTHER INFORMATION: n is a, c, g, or t

<400> SEQUENCE: 41

```
cgacgtaaaa cgacggccag tnnnnnnnnn nnnnnattat tgactctgtt gtgcttctat     60
tacag                                                                 65
```

<210> SEQ ID NO 42
<211> LENGTH: 50
<212> TYPE: DNA
<213> ORGANISM: Artificial sequence
<220> FEATURE:
<223> OTHER INFORMATION: Synthetic primer panel

<400> SEQUENCE: 42

```
cacacaggaa acagctatga ccatgacgtc actttcaaac gtgtatacac                50
```

<210> SEQ ID NO 43
<211> LENGTH: 62
<212> TYPE: DNA
<213> ORGANISM: Artificial sequence
<220> FEATURE:
<223> OTHER INFORMATION: Synthetic primer panel
<220> FEATURE:
<221> NAME/KEY: misc_feature
<222> LOCATION: (22)..(35)
<223> OTHER INFORMATION: n is a, c, g, or t

<400> SEQUENCE: 43

```
cgacgtaaaa cgacggccag tnnnnnnnnn nnnnnctaat agtgtattca cagagacttg     60
gc                                                                    62
```

-continued

```
<210> SEQ ID NO 44
<211> LENGTH: 48
<212> TYPE: DNA
<213> ORGANISM: Artificial sequence
<220> FEATURE:
<223> OTHER INFORMATION: Synthetic primer panel

<400> SEQUENCE: 44
cacacaggaa acagctatga ccatgtggct agaccaaaat cacaaatc                48

<210> SEQ ID NO 45
<211> LENGTH: 21
<212> TYPE: DNA
<213> ORGANISM: Artificial sequence
<220> FEATURE:
<223> OTHER INFORMATION: Synthetic M13 primer

<400> SEQUENCE: 45
cgacgtaaaa cgacggccag t                                             21

<210> SEQ ID NO 46
<211> LENGTH: 25
<212> TYPE: DNA
<213> ORGANISM: Artificial sequence
<220> FEATURE:
<223> OTHER INFORMATION: Synthetic M13 primer

<400> SEQUENCE: 46
cacacaggaa acagctatga ccatg                                         25

<210> SEQ ID NO 47
<211> LENGTH: 50
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (48)..(50)
<223> OTHER INFORMATION: Relevant residues are joined by a
      phosphodiester bond

<400> SEQUENCE: 47
aatgatacgg cgaccaccga gatctacacc gacgtaaaac gacggccagt              50

<210> SEQ ID NO 48
<211> LENGTH: 55
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (25)..(30)
<223> OTHER INFORMATION: n is a, c, g, or t
<220> FEATURE:
<221> NAME/KEY: misc_feature
<222> LOCATION: (53)..(55)
<223> OTHER INFORMATION: Relevant residues are joined by a
      phosphodiester bond

<400> SEQUENCE: 48
caagcagaag acggcatacg agatnnnnnn cacacaggaa acagctatga ccatg        55

<210> SEQ ID NO 49
<211> LENGTH: 2931
<212> TYPE: DNA
<213> ORGANISM: Homo sapien
```

```
<400> SEQUENCE: 49
atgagaggcg ctcgcggcgc ctgggatttt ctctgcgttc tgctcctact gcttcgcgtc        60
cagacaggct cttctcaacc atctgtgagt ccaggggaac cgtctccacc atccatccat       120
ccaggaaaat cagacttaat agtccgcgtg ggcgacgaga ttaggctgtt atgcactgat       180
ccgggctttg tcaaatggac ttttgagatc ctggatgaaa cgaatgagaa taagcagaat       240
gaatggatca cggaaaagc agaagccacc aacaccggca atacacgtg caccaacaaa         300 cacggcttaa gcaattccat ttatgtgttt gttagagatc ctgccaagct tttccttgtt       360
gaccgctcct tgtatgggaa agaagacaac gacacgctgg tccgctgtcc tctcacagac       420
ccagaagtga ccaattattc cctcaagggg tgccagggga agcctcttcc caaggacttg       480
aggtttattc ctgaccccaa ggcgggcatc atgatcaaaa gtgtgaaacg cgcctaccat       540
cggctctgtc tgcattgttc tgtggaccag gagggcaagt cagtgctgtc ggaaaaattc       600
atcctgaaag tgaggccagc cttcaaagct gtgcctgttg tgtctgtgtc caaagcaagc       660
tatcttctta gggaagggga agaattcaca gtgacgtgca caataaaaga tgtgtctagt       720
tctgtgtact caacgtggaa aagagaaaac agtcagacta aactacagga gaaatataat       780
agctggcatc acggtgactt caattatgaa cgttcaggca cgttgactat cagttcagcg       840
agagttaatg attctggagt gttcatgtgt tatgccaata atacttttgg atcagcaaat       900
gtcacaacaa ccttggaagt agtagataaa ggattcatta atatcttccc catgataaac       960
actacagtat ttgtaaacga tggagaaaat gtagatttga ttgttgaata tgaagcattc      1020
cccaaacctg aacaccagca gtggatctat atgaacagaa ccttcactga taatgggaa      1080 gattatccca gtctgagaa tgaaagtaat atcagatacg taagtgaact tcatctaacg       1140
agattaaaag gcaccgaagg aggcacttac acattcctag tgtccaattc tgacgtcaat       1200
gctgccatag catttaatgt ttatgtgaat acaaaccag aaatcctgac ttacgacagg       1260
ctcgtgaatg gcatgctcca atgtgtggca gcaggattcc cagagcccac aatagattgg      1320 tattttgtc caggaactga gcagagatgc tctgcttctg tactgccagt ggatgtgcag       1380
acactaaact catctgggcc accgtttgga aagctagtgg ttcagagttc tatagattct       1440
agtgcattca agcacaatgg cacggttgaa tgtaaggctt acaacgatgt gggcaagact       1500
tctgcctatt ttaactttgc atttaaaggt aacaacaaag agcaaatcca tcccacacc        1560 ctgttcactc ctttgctgat tggtttcgta atcgtagctg gcatgatgtg cattattgtg       1620
atgattctga cctacaaata tttacagaaa cccatgtatg aagtacagtg gaaggttgtt       1680
gaggagataa atggaaacaa ttatgtttac atagacccaa cacaacttcc ttatgatcac       1740
aaatgggagt ttccccagaaa caggctgagt tttgggaaaa cctgggtgc tggagctttc      1800 gggaaggttg ttgaggcaac tgcttatggc ttaattaagt cagatgcggc catgactgtc       1860
gctgtaaaga tgctcaagcc gagtgcccat ttgacagaac gggaagccct catgtctgaa       1920
ctcaaagtcc tgagttacct tggtaatcac atgaatattg tgaatctact ggagcctgc       1980 accattggag ggcccaccct ggtcattaca gaatattgtt gctatggtga tctttgaat      2040 ttttgagaa gaaacgtga ttcatttatt tgttcaaagc aggaagatca tgcagaagct       2100
gcactttata agaatcttct gcattcaaag gagtcttcct gcagcgatag tactaatgag       2160
tacatggaca tgaaacctgg agtttcttat gttgtcccaa ccaaggccga caaaaggaga       2220 tctgtgaaa taggctcata catagaaaga gatgtgactc ccgccatcat ggaggatgac       2280
gagttggccc tagacttaga agacttgctg agcttttctt accaggtggc aagggcatg      2340
```

```
gctttcctcg cctccaagaa ttgtattcac agagacttgg cagccagaaa tatcctcctt    2400
actcatggtc ggatcacaaa gatttgtgat tttggtctag ccagagacat caagaatgat    2460
tctaattatg tggttaaagg aaacgctcga ctacctgtga agtggatggc acctgaaagc    2520
attttcaact gtgtatacac gtttgaaagt gacgtctggt cctatgggat ttttctttgg    2580
gagctgttct ctttaggaag cagcccctat cctggaatgc cggtcgattc taagttctac    2640
aagatgatca aggaaggctt ccggatgctc agccctgaac acgcacctgc tgaaatgtat    2700
gacataatga agacttgctg ggatgcagat cccctaaaaa gaccaacatt caagcaaatt    2760
gttcagctaa ttgagaagca gatttcagag agcaccaatc atatttactc caacttagca    2820
aactgcagcc ccaaccgaca gaagcccgtg gtagaccatt ctgtgcggat caattctgtc    2880
ggcagcaccg cttcctcctc ccagcctctg cttgtgcacg acgatgtctg a             2931
```